(12) United States Patent
Klepper

(10) Patent No.: US 8,479,625 B2
(45) Date of Patent: Jul. 9, 2013

(54) METHOD TO MANUFACTURE A TUBE SUMP WITH INTEGRAL CLIPS

(76) Inventor: Mark S. Klepper, Austin, TX (US)

( * ) Notice: Subject to any disclaimer, the term of this patent is extended or adjusted under 35 U.S.C. 154(b) by 546 days.

(21) Appl. No.: 12/657,303

(22) Filed: Jan. 19, 2010

(65) Prior Publication Data

US 2010/0180737 A1     Jul. 22, 2010

Related U.S. Application Data

(60) Provisional application No. 61/205,500, filed on Jan. 21, 2009.

(51) Int. Cl.
*B26D 3/00* (2006.01)

(52) U.S. Cl.
USPC .................................. 83/39; 83/13

(58) Field of Classification Search
USPC ............. 83/39, 13; 607/92, 528; 128/207.15, 128/200.26, 207.14, 207.16; 606/142, 151, 606/192–196; 604/540, 41, 101.04, 96.01, 604/94.01, 264, 284, 523, 544; 15/244.1, 15/218.1, 246; 24/543, 335, 74.1, 74.2
See application file for complete search history.

(56) References Cited

U.S. PATENT DOCUMENTS

| | | | |
|---|---|---|---|
| 4,167,946 A * | 9/1979 | Sandstrom | 128/207.17 |
| 4,231,365 A | 11/1980 | Scarberry | |
| 4,453,353 A * | 6/1984 | Killop et al. | 52/147 |
| 4,716,615 A * | 1/1988 | Whitehead et al. | 15/220.4 |
| 4,786,812 A | 11/1988 | Humphreys | |
| 4,840,173 A | 6/1989 | Porter, III | |
| 5,009,227 A | 4/1991 | Nieuwstad | |
| 5,038,766 A | 8/1991 | Parker | |
| 5,067,497 A | 11/1991 | Greear et al. | |
| 5,241,956 A | 9/1993 | Brain | |
| 5,372,131 A | 12/1994 | Heinen, Jr. | |
| 5,501,215 A | 3/1996 | Huerta | |
| 5,513,627 A | 5/1996 | Flam | |
| 5,520,175 A | 5/1996 | Fry | |
| 5,588,424 A | 12/1996 | Insler et al. | |
| 5,637,877 A | 6/1997 | Sinofsky | |
| 5,819,723 A | 10/1998 | Joseph | |
| 5,855,203 A | 1/1999 | Matter | |
| 5,964,217 A | 10/1999 | Christopher | |
| 6,062,223 A | 5/2000 | Palazzo et al. | |
| 6,142,144 A | 11/2000 | Pacey | |
| 6,443,147 B1 | 9/2002 | Matter | |
| 6,460,540 B1 * | 10/2002 | Klepper | 128/207.14 |
| 6,470,888 B1 | 10/2002 | Matter | |
| 6,551,346 B2 | 4/2003 | Crossley | |
| 7,159,590 B2 | 1/2007 | Rife | |
| 2005/0039754 A1 * | 2/2005 | Simon | 128/207.14 |
| 2005/0120652 A1 * | 6/2005 | Cacciani et al. | 52/302.1 |
| 2007/0017527 A1 * | 1/2007 | Totz | 128/207.15 |

(Continued)

*Primary Examiner* — Ghassem Alie
(74) *Attorney, Agent, or Firm* — Paul M Denk

(57) ABSTRACT

A method of making a tube sump with integral clips from a single material modifies multiple lumen tubing of any material that allows for two or more lumens. Preferably, the tubing is a plastic polymer with dual lumens. One lumen functions as a suction tube and the other lumen undergoes modification to form tubular clips. The modification removes a pattern of tubing opposite the suction tube to form integral clips that retain the tube sump upon an existing endotracheal tube. The removed sections of lumen may have any length or number. Common methods to remove the lumen sections include mechanical cutting, sawing, laser cutting, thermal cutting, melting, ablating, and shearing. Alternatively, the clips may be formed during the manufacture of the multiple lumen tubular product.

14 Claims, 3 Drawing Sheets

U.S. PATENT DOCUMENTS

| | | | |
|---|---|---|---|
| 2007/0106122 A1* | 5/2007 | Yokota et al. | 600/188 |
| 2008/0159908 A1 | 7/2008 | Redmond | |
| 2008/0257355 A1 | 10/2008 | Rao | |
| 2008/0306454 A1 | 12/2008 | Sikora | |

* cited by examiner

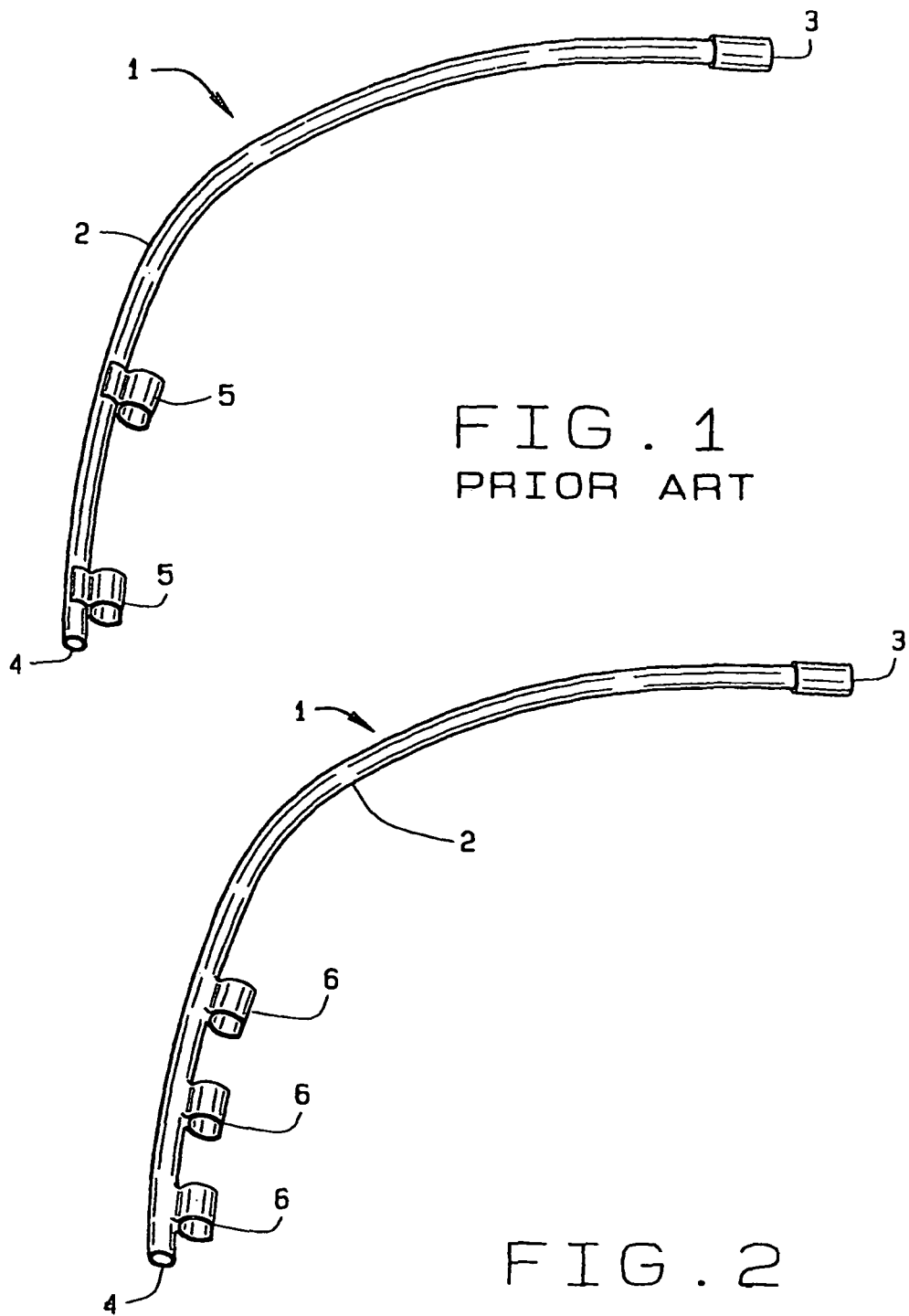

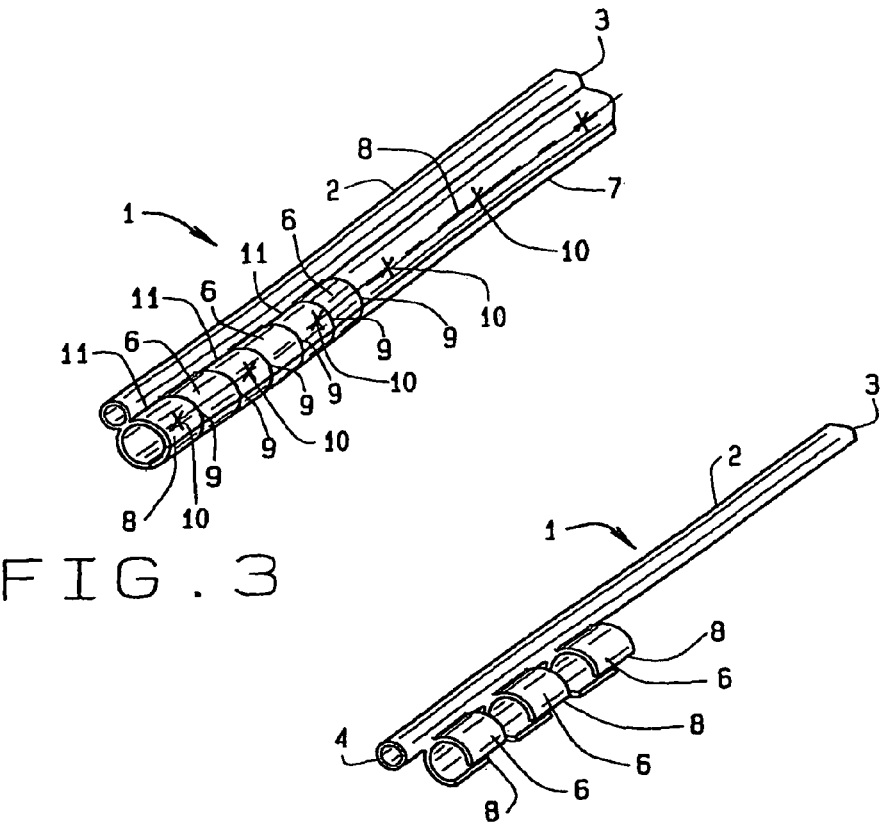
FIG. 3
FIG. 4
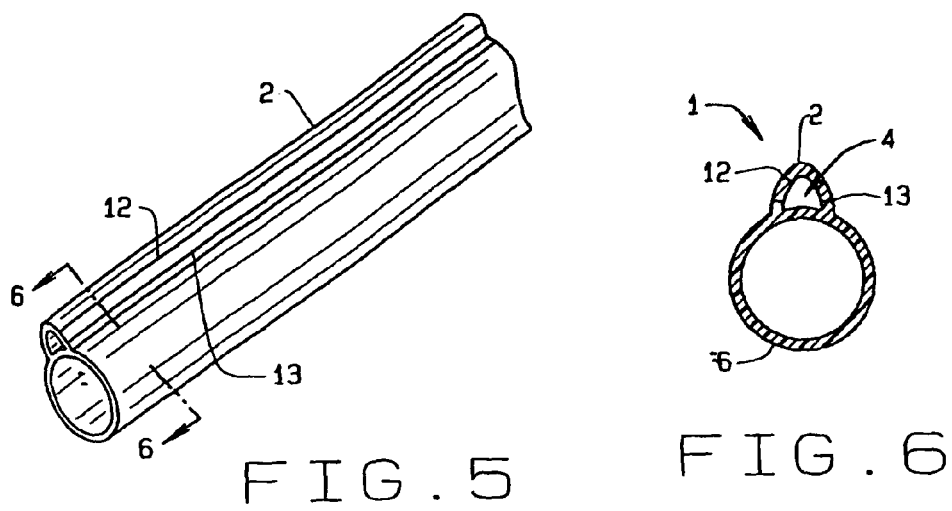
FIG. 5
FIG. 6

METHOD TO MANUFACTURE A TUBE SUMP WITH INTEGRAL CLIPS

CROSS REFERENCE TO RELATED APPLICATION

This non provisional patent application claims priority to the provisional patent application having Ser. No. 61/205,500, having filing date Jan. 21, 2009.

BACKGROUND OF THE INVENTION

The present invention relates to tubular medical devices and more particularly to making a tube sump simultaneously with integral clips where the clips connect the tube sump to another tube.

A patient presents to a medical practitioner with any of a host of symptoms or conditions. Generally the practitioner checks for life threatening symptoms or conditions and then shifts patient intake to more chronic ailments. Life threatening conditions generally affect the airway, breathing, or circulation. Circulation conditions receive various cardiac treatments. Airway and breathing conditions call for measures to restore or to improve the air flow into the respiratory system, usually through the trachea. In the setting of respiratory failure, an artificial airway in the form of a tube may be inserted into the patient's pharynx and then the trachea. The tube can then provide air flow to the lungs under their own power or upon a ventilator. Beyond respiratory conditions, tubes also see usage in treating digestive conditions where a component of the digestive tract requires a supported reopening. Tubes used for respiratory or digestive conditions remain open and allow for air or digestive matter to pass through. However, tubes at times provide an eddy at their ends where infection vectors or digestive matter may collect. Such vectors and matter lead to infections that require additional care.

A tube sump has been developed and connects to ventilation, tracheal, and endotracheal tubes among others. The tube sumps have a flexible, elongated, hollow main body and then a plurality of separate clips or clamps attached to the main body. The hollow main body allows for suction to drain any infection vectors or digestive matter that accumulates at the end of a tube within a patient. Prior art tube sumps generally have a multiple step manufacturing process that mates a catheter like component to separate clip structures. The clips and catheter component attach using various methods known to the art. However, these methods of manufacture called for separate pieces subject to engineering and manufacturing, and a strong and durable attachment of the clips to the suction catheter while yielding a somewhat wide profile tube sump that encountered a more difficult passage through the upper airway of patients.

Various manufacturing methods have produced bundled tubes, or lumens, for many applications. The present invention though focuses upon a two lumen extrusion that meets the narrow profile required for placement into a patient's natural airway. The two lumen extrusion can then be modified to have clips thereon for grasping an adjacent tube, such as an artificial airway. Medical device manufacturers have shown some interest in further tube sump developments, such as Zeus Industrial Products, Inc., of Orangeburg, S.C.

DESCRIPTION OF THE PRIOR ART

Tube sumps have been develop in many forms in the prior art. The U.S. Pat. No. 6,460,540 to Klepper has an endotracheal tube sump that included a suction tube, or catheter, used to evacuate material from the airway of humans. This suction tube connected to a suction generating device on one end and vacuumed material into the suction tube via one or more openings at the opposite end. This suction tube enters the upper airway of a patient through the mouth as it is attached to and follows an existing ventilatory support tube, or endotracheal tube, ETT. The suction tube has connectors that consist of circular clips. These clips are then attached to the suction tube as incomplete tubular structures that can warp around the ventilatory tube and are then advanced by sliding along the course of the ventilating tube. However, the tube and clips remain separate components that require mutual attachment prior to placement within a patient.

The present invention overcomes the difficulties of the prior art. The present invention uses double lumen, or tubular, material that has one lumen cut into sections. Unnecessary sections are then removed leaving a plurality of spaced apart sections or clips opposite a complete lumen, or tube. The method of the present invention results in a tubular structure with integral clips.

SUMMARY OF THE INVENTION

The present invention provides a method of making a tube sump with integral clips from a single material without separate components. The method of the present invention involves multiple lumen tubing of any material compatible with the requirements of the finished product. The tubing may be extruded, or produced, by known means that allow for two or more lumens of any size or shape. The lumen dimensions then match the purpose specific to a suction catheter with clips. Preferably, the tubing is a plastic polymer extruded as dual lumen tubing. One of the lumens or tubes is a suction tube and the other lumen, contiguous with the suction tube, undergoes modification to form tubular clips.

The modification removes a pattern of tubing opposite the suction tube to form an overall tubular device with integral tubular retaining structures, or clips. The removed sections of lumen may have any length or number and involve one or both lumens for attachment upon various medical devices such as tracheal tubes, endotracheal tubes, esophageal tubes, and the like. The sections of lumen are removed following initial manufacture of the multiple lumen material using known manufacturing methods, such as extrusion. The most common methods foreseen for the invention to remove the lumen sections include mechanical cutting, sawing, laser cutting, thermal cutting, melting, abating, shearing, and the like. Alternatively the clips, or subtractions of tube, may be formed during the manufacture of the multiple lumen tubular product.

The method of the present invention involves tubular materials with two or more lumens or passages and creates various combinations of intact tubular structures and clips composed of the remaining adjacent tubing. The present invention produces an endotracheal sump, ETS, that has a main suction tube and several, approximately ½ inch long, curved structures, or clips, spaced one to two inches apart longitudinally along the ETS and concentrated on the end of the ETS that engages an ETT. The main suction tube then evacuates secretions and other matter from the posterior pharynx and subglottic space of a patient.

There has thus been outlined, rather broadly, the more important features of the invention in order that the detailed description thereof that follows may be better understood and that the present contribution to the art may be better appreciated. In the preferred form, the method of the present invention cuts and removes sections of a second lumen in a pattern from a contiguous first lumen. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

It is an object of the present invention to provide a method of manufacturing a tube sump, such as an endotracheal sump, from dual lumen material where one lumen is cut into a pattern of clips.

It is another object of the present invention to avoid bonding a separate clip to a suction tube.

It is another object of the present invention to have its tubular components being integral with its clips.

It is another object of the present invention to allow for ready alteration of the profile of the suction tube, or bending.

It is another object of the present invention to allow for ready substitution of clip thicknesses and suction tube wall thickness for useful variations in gripping strength of tube sumps resulting from the present invention.

It is another object of the present invention to lend itself to automated production.

It is another object of the present invention to provide a finished product with a minimum of production steps.

It is another object of the present invention to provide a method resulting in clips that open transverse to the suction tube for manual placement of the suction tube upon an ETT.

It is another object of the present invention to permit longitudinal cutting or slitting during manufacturing.

It is another object of the present invention to introduce enhancements into the suction tube or clips by selective trimming of multiple lumen tubing.

It is another object of the present invention to support placement of fiber optics, electrical, radiological, and other elongated devices upon the multiple lumen tubing.

It is another object of the present invention to provide clips that grasp additional tubes of alternate sizes and shapes that the initial suction tube.

It is another object of the present invention to provide a new and improved method to manufacture a tube sump with integral clips that may be easily and efficiently setup and operated at lower cost than existing manufacturing methods.

Further objects and advantages of the subject invention will be apparent to those skilled in the art. These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings,

FIG. 1 illustrates a prior art catheter with attached guide clips;

FIG. 2 shows a catheter manufactured following the present invention where the clips are integral with the remaining tube;

FIG. 3 shows a dual lumen tube marked for forming clips;

FIG. 4 provides a dual lumen tube with material removed thus leaving integral clips;

FIG. 5 describes an alternate embodiment of the dual lumen tube where the suction lumen also includes embedded linear features; and, FIG. 6 shows a cross section of the tip of the alternate embodiment.

The same reference numerals refer to the same parts throughout the various figures.

DETAILED DESCRIPTION OF THE INVENTION

Figure 7:
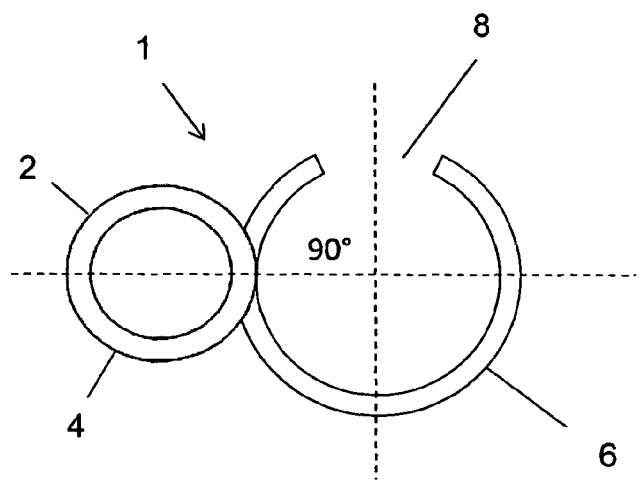
FIG. 7 is an end view of one embodiment having the slit formed and centered at approximately 90° in rotation away from the catheter.

The present invention provides a method of manufacturing a tube sump for insertion within a patient generally upon existing endotracheal tubes ETT or other tubular devices. An existing tube sump 1 of the Applicant, U.S. Pat. No. 6,460,540, is shown in FIG. 1. The tube sump 1 has a tube like catheter 2 that generally flexes and bends and has two opposite ends. Upon one end, the catheter has a fitting 3 for connecting the tube sump to a suction line or other medical device. And on the opposite end, the catheter has an open tip 4 that allows for collection and withdrawal of secretions and other matter through the catheter. Because the catheter flexes and bends, the catheter may deflect upon the structures of a patient's pharynx and miss insertion into the trachea, esophagus, or other desired organ. The patented tube sump of the Applicant provides at least one, preferably two, clips 5 separately made from the catheter. Each clip generally has an interrupted figure eight like cross section with a small end and an opposite large end. The large end has two jaws that allow the clip to grip an ETT or other tubular devices as selected by the medical staff. The small end has two lesser jaws that deflect outwardly and slip upon the catheter. In a typical application, shown in FIG. 1, one clip is located proximate the tip 3 and a second clip is located about one third the length of the catheter away from the tip. The clips can be relocated by the medical staff by manipulating the lesser jaws of a clip's small end.

As described above, the tube sump utilizes separate clips that require the medical staff to locate the clips upon the catheter and that may slide somewhat when lubricated by bodily fluids upon insertion within a patient. The method of the present invention produces a tube sump with integral clips that do not slide along a catheter as shown in FIG. 2. The tube sump from the present invention has a catheter 2 with a fitting 3 and an opposite tip 4 as before. This tube sump though has at least two integral clips 6, here shown as three. These clips 6 have a generally round cross section and a C like shape with the opening of the C like shape being approximately 90° to the catheter portion of the tube sump as shown in FIG. 2 and in FIG. 7.

Figure 8:
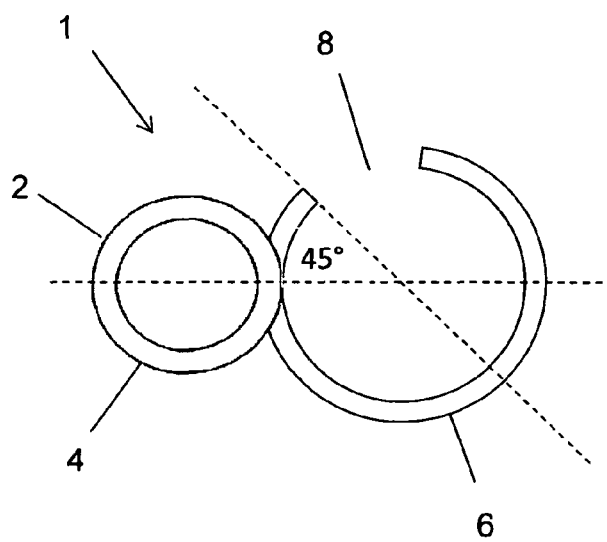
FIG. 8 is an end view of another embodiment having the slit formed at slightly over 45° in rotation from the catheter.

The present invention begins with a dual lumen tube as shown in FIG. 3 and produced upon existing machinery. The tube may have various luminal moieties. One lumen serves as a catheter 2 and the opposite lumen 7 provides the material and rough structure for clips 6. The catheter 2 is generally integral with the opposite lumen 7 along the entire length of the catheter 2 at the beginning of the present invention. The present invention then provides a longitudinal slit or slot as at 8 along the length of the opposite lumen 7. The slit 8 is generally 90° in rotation away from the catheter 2 though other angular positions, such as 180° in rotation away from the catheter 2, as shown in FIG. 4, are foreseen by the Applicant. Preferable, however, the slit will be at least 45° in rotation away from the catheter, as shown in FIG. 8. Then the present invention has a series of lateral cuts made into the opposite lumen 7 along the lines as at 9. The lateral cuts only penetrate the opposite lumen 7, not the catheter 2. The lateral cuts result in the clips 6 locating within portions of the opposite lumen 7, marked for lateral removal as at 10. In an alternate embodiment, the removable portions 10 of the opposite lumen 7 are further cut along their common joint, as at 11, with the catheter 2. This cut, as at 11, ends slightly short of a complete cut so that the portion can remain in place until removed by medical staff as desired.

As can be observed from FIG. 4, such operations effect the desired resulting integral clips 6, which have a C like shape, as has been discussed hereinabove, with the slit 8 sized to from the desired opening in the C like shape. Such opening in the formed integral clips 6 then permits the resulting law portions on opposite sides of the slit 8 to engage a separate medical procedure tube inserted into the slit 8 and to clamp the tube sump construction 1 to the other medical procedure tube, similarly to the manner in which the separate clips 5 of the prior art construction of FIG. 1 permit the catheter 2 thereof to be attached to a separate other medical procedure tube, as is also discussed in applicant's above noted U.S. Pat. No. 6,460, 540.

Once the cuts are made in the opposite lumen, as at 8, 9, and 11, the manufacturer, or the medical staff, can dislodge the removable portions, leaving clips 6 in desired locations as in FIG. 4. The cuts of the present invention leave intact clips with a slit opening at a desired spaced interval. And further, the clips are integral with the catheter 2. The medical staff need not attach a separate clip to a catheter as in the prior art. With the portions 10 removed, the tube sump manufactured by the method of the present invention is ready for immediate usage.

An alternate embodiment of the present invention is shown from the side in FIG. 5 and from the end in FIG. 6. The alternate embodiment modifies a dual lumen tube primarily in the vicinity of the catheter 2, not the opposite lumen 7. The catheter has embedded within it at least one line, wire 12, or conduit 13. The line may deliver electrical power as through the wire, suction, air, water, and the like to the tip while the conduit may deliver laser light of various wavelengths, visible light, ultraviolet light, infra red light, or similar energy, either directly or through a fiber optic cable. Though the catheter has the embedded wire, the opposite lumen 7 remains available for cutting and slitting to form clips 6 as previously described. FIG. 6 shows the tip 3 of the alternate embodiment where the ends of the wire 12 or the conduit 13 deliver their contents to the patient proximate the tip of a tube sump.

The invention has been described herein with the reference to certain preferred embodiments. It is understood that obvious variants thereon will become apparent to those skilled in the art. The invention is not to be considered as limited thereto.

From the aforementioned description, a method to manufacture a tube sump with integral clips has been described. The method is uniquely capable of transforming a dual lumen tube into a tube sump with integral fixed clips. The manufacturing method may be performed upon many materials, including but not limited to, polymers, polyethylene, polypropylene, nylon, ferrous and non-ferrous metals and the alloys, and composites.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A process for forming a tubular construction that includes a plurality of spaced integral clips for attaching such tubular construction to a separate longitudinal medical procedure tubular device for use as a tube sump attachable to such medical procedure tubular device, comprising:

providing a longitudinally extending tube having:
a distal end and a proximal end;
at least two lumens extending generally longitudinally through said tube in a generally side-by-side relationship, one of said lumens, defined as a first lumen, configured to be employable as a tube sump and another of said lumens, defined as a second lumen, being available for other uses;
an intermediate wall separating said first and second lumens;
an outer wall surrounding said lumens and said intermediate wall;
said tube, when disposed towards a user with said first and second lumens disposed generally laterally side-by-side, presenting a front tube face and a front tube face view of said tube to the user and, when disposed towards a user with one of said lumens disposed generally forwardly of the other of said lumens, presenting a tube side and tube side view of said tube to the user, said tube face so presented in said tube face view defined to be said front face of said tube, said tube also having a back tube face generally opposite said front face;
forming along and exterior to said first lumen at least a pair of spaced integral clips that project laterally sidewardly from said intermediate wall by:
positioning and aligning said tube for cutting;
cutting a longitudinal slot in said tube, said slot extending through the outer wall adjacent said second lumen into said selected lumen second lumen, the formation of said longitudinal slot effecting a slot opening in said outer wall adjacent said second lumen that separates the wall segments on opposite sides of said slot from one another and forms separated first and second jaw portions on the opposite sides of said slot;
cutting into said tube a lateral cut pattern the individual lateral cuts of which extend generally laterally into said tube from a tube side through said outer wall of said tube adjacent said second lumen into said second lumen towards said intermediate wall between said two lumens, said lateral cuts extending generally cross-ways relative to the longitudinal slot and terminating before penetrating said first lumen, generally along said intermediate wall, said lateral cut pattern including at least a first lateral cut defining a gap in said outer wall adjacent said first lumen between a first outer wall segment above, said gap and a second outer wall segment below said gap, said gap having a length along said tube greater than the longitudinal dimensions of said first and second wall segments, said first outer wall segment with said longitudinal slot therealong having a portion forming a first integral clip nearer said proximal end of said tube and said second outer wall segment with said longitudinal slot therealong having a portion forming a second integral clip nearer said distal end of said tube and spaced from said first integral clip; and
whereby said resulting construction is a longitudinal tubular construction with said first lumen extending therethrough and with spaced integral clips formed thereal ong extending laterally sidewardly therefrom, said integral clips each including said first and second jaw portions formed from the separated wall segments on the opposite sides of said longitudinal slot, said jaw portions flexibly operable to permit a medical procedure tube to be extending laterally through said slot opening, and also to engage the portion of the medical procedure tube inserted through said slot opening in said integral clips to thereby position and hold said tubular construction along and adjacent to the medical procedure tube.

2. The process of claim 1, wherein cutting a longitudinal slot effects formation of said slot opening at least 45° in rotation away from said front tube face of said tube.

3. The process of claim 2 wherein said longitudinal slot is cut approximately 90° in rotation from said front tube face of said tube.

4. The process of claim 2 wherein said longitudinal slot is cut approximately 180° in rotation from said front tube face of said tube.

5. The process of claim 1, wherein said process results in a catheter with integral round clips spaced therealono and projecting laterally sidewardly therefrom.

6. The process of claim 1, wherein said process is performable upon tubes with various sizes and shapes of luminal moieties.

7. The process of claim 1 wherein:
said lateral cut pattern includes a plurality of lateral cuts;
said plurality of lateral cuts include top and bottom cuts adjacent the proximal and distal ends of said tube;
said top cut defines a proximal end spacing extending between said proximal end of said tube and the top of the remaining segment of said outer wall; and
said bottom cut defines a distal end spacing between said distal end of said tube and the bottom of the remaining segment of said outer wall.

8. The process of claim 7 wherein:
said first lateral cut is an intermediate cut spaced between said top and bottom cuts, and the outer wall segments remaining between said top, intermediate, and bottom cuts form a pair of spaced integral clips.

9. The process of claim 8 wherein:
said bottom cut of said first cut pair is said upper cut; and
said top cut of said second cut pair is said lower cut.

10. The process of claim 7 further including:
making a proximal end separation cut extending longitudinally along said tube from said proximal end of said tube to said top cut of said first cut pair; and
making a distal end separation cut extending longitudinally along said tube from said bottom cut of said second cut pair to said distal end of said tube.

11. The process of claim 10 further including:
making separation cuts between the bottom cut of a given cut pair and the top cut of an adjacent cut pair.

12. The process of claim 11 wherein:
said cut pairs include at least three cut pairs; and
said formed integral clips are spaced along said first lumen from near said proximal end to near said distal end of said tube.

13. The process of claim 1 wherein:
removing said disposable portions of said tube includes making one or more separation cuts in said tube extending from the front tube face to the back face of said tube through said intermediate wall of said tube and generally longitudinally along said intermediate wall to separate said tube, as defined by said separation cuts, into one or more disposable portions of said tube and a remainder portion of said tube; and
said separation cuts include a first separation cut extending generally longitudinally along said tube between said upper and lower lateral cuts.

14. The process of claim 1 wherein said lateral cuts are substantially perpendicular to the longitudinally extending tube.

\* \* \* \* \*